US00PP28597P3

(12) United States Plant Patent
Gerdts et al.

(10) Patent No.: US PP28,597 P3
(45) Date of Patent: Nov. 7, 2017

(54) PEACH TREE NAMED 'BURPEACHTHIRTYSEVEN'

(50) Latin Name: *Prunus persica*
Varietal Denomination: Burpeachthirtyseven

(71) Applicants: Timothy J. Gerdts, Kingsburg, CA (US); John K. Slaughter, Fresno, CA (US)

(72) Inventors: Timothy J. Gerdts, Kingsburg, CA (US); John K. Slaughter, Fresno, CA (US)

(73) Assignee: The Burchell Nursery, Inc., Oakdale, CA (US)

( * ) Notice: Subject to any disclaimer, the term of this patent is extended or adjusted under 35 U.S.C. 154(b) by 48 days.

(21) Appl. No.: 14/998,398

(22) Filed: Dec. 31, 2015

(65) Prior Publication Data

US 2017/0196135 P1 Jul. 6, 2017

(51) Int. Cl.
*A01H 5/08* (2006.01)

(52) U.S. Cl.
USPC ..... Plt./197

(58) Field of Classification Search
USPC ..... Plt./197, 198
CPC ..... A01H 5/0868; A01H 5/08; A01H 5/0856
See application file for complete search history.

*Primary Examiner* — June Hwu
(74) *Attorney, Agent, or Firm* — Randall Danskin, P.S.

(57) ABSTRACT

A new and distinct variety of peach tree is described and which is denominated varietally as 'Burpeachthirtyseven', and which produces an attractively colored yellow fleshed, clingstone peach which is mature for harvesting and shipment approximately September 23 to September 29 under the ecological conditions prevailing in the San Joaquin Valley of central California.

1 Drawing Sheet

Latin name: '*Prunus persica*'.
Varietal denomination: 'Burpeachthirtyseven'.

BACKGROUND OF THE NEW VARIETY

The present variety of peach tree resulted from an ongoing program of fruit and nut tree breeding. The purpose of this program is to improve the commercial quality of deciduous fruit and nut varieties, and rootstocks, by creating and releasing promising selections of *Prunus, Malus, Punica* and *Juglans* species. To this end we make both controlled and hybrid cross pollinations each year in order to produce seedling populations from which improved progenies are evaluated and selected.

The seedling, 'Burpeachthirtyseven' was originated by us, and selected from a population of seedlings growing in our experimental orchards which are located near Fowler, Calif. The seedlings, which were grown on their own roots, were derived from planting seed derived from the 'Fayette' peach tree, and which is a USDA-released, (unpatented) commercially-planted yellow peach. The pollen parent was an unnamed and unpatented selection which is owned by the Assignee of the present plant patent application. Fruit was collected from the female parent and seeds were extracted. After a period of stratification, the resulting seed was placed in a greenhouse, by population, and then field planted for tree establishment, and ultimately to exhibit fruit for subsequent evaluation. One yellow fleshed peach seedling, which is the present variety, exhibited especially desirable characteristics, and was then designated as 'C11.012'. This peach seedling was marked for subsequent observation. After the 2006 fruiting season, the new variety of peach tree was selected for advanced evaluation, and repropagation.

ASEXUAL REPRODUCTION

Asexual reproduction of this new and distinct variety of peach tree was accomplished by budding the new peach tree onto 'Nemaguard' Rootstock (un-patented). This was performed by us in our experimental orchard which is located near Fowler, Calif. Subsequent evaluations of these asexually reproduced plants have shown those asexual reproductions run true to the original tree. All characteristics of the original tree, and its fruit, were established, and appear to be transmitted through these succeeding asexual propagations.

SUMMARY OF VARIETY

'Burpeachthirtyseven' is a new and distinct variety of peach tree, which is considered of relatively large size, and which has a vigorous growth characteristic. This new tree is also a regular and productive bearer of relatively large, firm, yellow-fleshed, acidic, clingstone fruit which have a very good flavor, and eating qualities. This new peach tree has a medium chilling requirement of approximately 650 hours, and further produces relatively uniformly sized fruit throughout the tree's canopy. In addition to the foregoing, the fruit of the new peach tree also appears to have good handling, and shipping qualities. The 'Burpeachthirtyseven' peach tree bears fruit which are typically ripe for commercial harvesting and shipment on approximately September 23 to September 29 under the ecological conditions prevailing in the San Joaquin Valley of central California. In relative comparison to the 'Autumn Rose' peach tree (U.S. Pat. No. 7,990), and which is the closest known variety, the new variety of peach tree bears fruit that ripens 5-7 or more days later, and the current variety exhibits a more rounded shape especially at the apex. Further, the current variety exhibits a higher percentage of reddish blush on the surface of the fruit. Additionally the current variety is a true clingstone which is different from the closest comparator. Further the present new variety is distinguishable from the seed parent 'Fayette' by producing fruit which are ripe for harvesting and shipment about 6 weeks later than fruit produced by the 'Fayette' variety at the same geographical location.

BRIEF DESCRIPTION OF THE DRAWINGS

The accompanying drawing, which is provided, is a color photograph of the fruit produced by the new peach variety. The photograph depicts two whole mature fruit which are viewed from the apical and basal aspects. Additionally one mature fruit is bisected in the sagittal or sutural plane, and which displays the flesh color, and the exposed stone characteristics thereof. The external coloration of the fruit as shown in the photograph is sufficiently matured for harvesting and shipment. The colors in the photograph as provided are as nearly true as is reasonably possible in a color representation of this type. Due to chemical development, processing and printing, the color of the fruit depicted in this photograph may, or may not, be accurate when compared to the actual specimen. For this reason, future color references should be made to the color plates (Royal Horticultural Society, Fourth Edition, 2001), and the descriptions as provided, hereinafter.

NOT A COMMERCIAL WARRANTY

The following detailed description has been prepared to solely comply with the provisions of 35 U.S.C. §112, and does not constitute a commercial warranty, (either expressed or implied), that the present variety will, in the future, display all the botanical, pomological or other characteristics as set forth, hereinafter. Therefore, this disclosure may not be relied upon to support any future legal claims including, but not limited to, breach of warranty of merchantability, or fitness for any particular purpose, or non-infringement which is directed, in whole, or in part, to the present variety.

DETAILED DESCRIPTION

Referring more specifically to the pomological details of this new and distinct variety of peach tree, the following has been observed during the 8th fruiting season, and under the ecological conditions prevailing at the orchards of the assignee and which are located near the town of Fowler, county of Fresno, state of California. All major color code designations are by reference to The R.H.S. Colour Chart (Fourth Edition, 2001), and which is provided by The Royal Horticultural Society of Great Britain. Common color names are also occasionally used.

TREE

Size: Generally considered medium to medium-large in its growth pattern as compared to other common commercial peach cultivars ripening in the late season of maturity. The tree of the present variety was pruned to a height of approximately 270.0 cm. to about 310.0 cm. at commercial maturity.

Tree width: Approximately 285.0 cm.

Tree vigor: Considered moderately vigorous. The present peach tree variety grew from about 170.0 cm. to about 180.0 cm. in height during the first growing season. The new variety was pruned to a height of approximately 150.0 cm. during the first dormant season, and primary scaffolds were then selected for the desired tree structure.

Fruit productivity: Productive. Fruit set varies from more than the desired crop load, to levels higher than the desired amounts, when the new variety is grown in a suitable horticultural zone, and under appropriate commercial nursery conditions. The fruit set is spaced by thinning to develop the remaining fruit into the desired market-sized fruit. The number of the fruit set varies with the prevailing climatic conditions, and the horticultural practices which are employed.

Fruit bearing: Regular. Fruit set has been more than adequate during the previous years of observation, and thinning was necessary during the past 8 years on both the original seedling, and on subsequent, asexually reproduced trees.

Tree form: Upright, and pruned into a vase-like shape.

Tree density: Considered moderately dense. It has been discovered that pruning the branches from the center of the tree to obtain a resulting vase-like shape allows for enhanced air movement, and appropriate amounts of sunlight to be received so as to improve fruit color, and renewal of fruiting wood, throughout the tree.

Chilling requirement: The present tree was grown and evaluated in USDA Hardiness Zone 9. The calculated winter chilling requirements of the new tree is approximately 650 hours at a temperature below 7.0 degrees C.

Hardiness: The present variety of peach tree appears to be hardy under typical, central San Joaquin Valley climatic conditions.

TRUNK

Trunk diameter: Approximately 17.5 cm in diameter when measured at a distance of approximately 15.24 cm. above the soil level. This measurement was taken at the end of the 8th growing season.

Bark texture: Considered moderately rough, and displaying folds of papery scarfskin. Since bark development and coloration change with advancing tree age, this characteristic varies with the tree vigor, age and regional conditions. Therefore, this is not a dependable descriptor of the new variety.

Trunk lenticels: Flat, oval lenticels are present, but are not abundant. The lenticels range in size from approximately 4.0 millimeters, to about 6.0 mm. in width, and between about 2.0 and about 3.0 millimeters, in height. The development and size of the trunk lenticels can be influenced, to some degree, by the ambient growing conditions, and are not, necessarily, a dependable characteristic of this new variety. As trees of this variety mature, lenticels are present, but they are generally covered by increasing layers of cork (mature bark) and therefore become less apparent to an observer.

Lenticel color: Considered an orange brown, (RHS Greyed-Orange Group N167 A).

Bark coloration: Variable, but it is generally considered to be a grey-brown, (RHS Grey-Brown Group N200 B). This bark coloration description was taken from trees in their seventh leaf which have ruptured the scarf skin, and which also have developed bark furrowing which is much more typical of the bark of older trees. It should be noted that the coloration of the bark is influenced, and varies, as the smoother, darker background color approaches other bark features such as the lenticels, and the initial fissures which form a feature of the scarf skin development.

BRANCHES

Branch size: Considered medium large for the variety.

Branch diameter: Average as compared to other peach varieties. The branches have a diameter of about 12.0 centimeters when measured during the 8th year after grafting.

Surface texture: Average, and appearing furrowed on wood which is several years old.

Crotch angles: Primary branches are considered variable, and are usually found growing at an angle of about 46 to about 55 degrees, when this characteristic is measured from a horizontal plane. This tree characteristic can be influenced, to some degree, by tree vigor, rootstock and other horticultural conditions which are employed.

Current season shoots:

*Surface texture.*—Substantially glabrous.

Internode length: Approximately 2.6 cm.

Color of mature branches: Approximately grey brown, (RHS Greyed-Brown Group 199 A).

Current season's shoots:

*Color.*—Medium green, (RHS Green Group 144 A). The color of new shoot tips is considered a bright and shiny green, (RHS Yellow-Green Group 146 D). The vegetative shoot color can be significantly influenced by plant nutrition, irrigation practices, and exposure to sunlight, and therefore should not be considered a consistent botanical characteristic of this new peach tree variety.

LEAVES

Size: Considered medium-large for the species. Leaf measurements have been taken from vigorous, upright, current-season growth, at approximately mid-shoot. It should be understood that the leaf size is often influenced by prevailing growing conditions, quality of sunlight, and the location of the leaf within the tree canopy. For this reason, leaf sizes can vary significantly based upon the ambient and other horticultural factors, listed above, and are not typically considered a dependable botanical descriptor.

Leaf length: Approximately 159.0 to about 172.0 millimeters.

Leaf width: Approximately 32.0 to about 35.0 millimeters.

Leaf base-shape: The leaves generally exhibit equal marginal symmetry relative to the leaf longitudinal axis.

Leaf form: Lanceolate.

Leaf tip form: Acuminate.

Leaf color:

*Upper leaf surface.*—A dark yellow-green, (approximately RHS Yellow-Green Group 146 A).

Leaf texture: Both upper and lower leaf surface textures are considered glabrous.

Leaf color:

*Lower leaf surface.*—A light to medium green, (approximately RHS Yellow-Green Group 146 B).

Leaf venation: Pinnately veined.

Mid-vein:

*Color.*—Considered a light yellow, (approximately RHS Greyed-Yellow Group 160 A) when observed in the early to mid-period of the growing season. The Mid-Vein is descriptive of the ventral side. The lower surface of this portion of the leaf does not exhibit red coloration.

Leaf margins:

*Shape.*—Gently undulating.

*Marginal form.*—Considered finely crenate.

*Marginal uniformity.*—Considered generally uniform.

Leaf petioles:

*Form.*—Considered canaliculated, and having a more pronounced trough when viewed from the dorsal aspect. The petiole margin is considered rounded when viewed from the ventral aspect.

*Size.*—Considered medium-small for the species.

*Length.*—About 6.0 to about 9.0 mm.

*Diameter.*—About 1.5 to about 2.0 mm.

*Color.*—Light yellow green, (approximately RHS Yellow-Green Group 145 C).

Leaf glands:

*Size.*—Considered small for the species; approximately 1.5 mm. in length; and about 1.0 mm. in height.

*Leaf glands.*—Numbers — Generally one and less commonly two glands appear per marginal side. Observations of more than two glands per marginal side are very uncommon,

*Gland type.*—Glands located at the base of the leaf are predominantly reniform in shape. An additional one to two, or occasionally more glands, which appear globose, and stalked, are often present at the basal margin of the leaf petiole, as well.

*Leaf gland color.*—Considered a medium-dark brown, approximately (RHS Brown Group N199 C). Typically the coloration of the leaf glands darken, and occasionally begin to desiccate during, and thereafter, in the mid-late growing season.

Leaf stipules:

*Size.*—Medium for this variety generally 6.0-8.0 mm.

*Number.*—Typically 2 per leaf bud, and up to 6 per shoot tip.

*Form.*—Lanceolate in form, and having a serrated marginal edge.

*Color.*—Green, (approximately RHS Green Group 137 B) when young, but graduating to a brown color, (approximately RHS Greyed-Orange Group 164 A) with advancing senescence. The leaf stipules are generally considered to be early deciduous.

FLOWER BUDS

Hardiness: No winter injury (bud death) has been noted during the last several years of observation under the ecological conditions prevailing in the central San Joaquin Valley. The new variety of peach tree has not been intentionally subjected to drought, cold or heat stress, and therefore this information is not available.

Flower bud:

*Size.*—Variable, and dependent on the state of maturity. The flower buds, as described, were observed approximately 7 days prior to bloom.

Flower bud:

*Length.*—Approximately 15.0 millimeters.

Flower bud:

*Diameter.*—Approximately 9.0 millimeters.

Flower bud surface texture: Pubescent.

Flower bud orientation: Considered appressed, but appearing less so as the blossoms near the time for opening.

Bud scale color: Approximately RHS Greyed-Purple 185 C.

Beginning of leaf bud burst is medium-late.

Density of flower buds along the current year's shoots. Flower bud density is medium density, and is more than adequate for commercial fruit production.

FLOWERS

Date of first bloom: Observed on Feb. 27, 2015.

Blooming time: Considered average in relative comparison to other commercial peach cultivars which are grown in the central San Joaquin Valley. The date of full bloom was observed on Mar. 4, 2015. The date of full bloom varies slightly with climatic conditions, and prevailing horticultural practices.

Duration of bloom: Approximately 9 or more days. This particular characteristic varies slightly with the prevailing climatic conditions.

Flower class: Considered a perfect flower, complete and perigynous.

Flower type: The variety is considered to have a showy type flower.

Flower size: Considered medium. The flower diameter at full bloom, is approximately 34.0 to 38.0 millimeters.

Bloom quantity: Considered abundant.

Flower bud frequency: Generally two flower buds appear per node, occasionally one flower bud per node is observed.

Petal size: Generally considered medium for the species.

*Petal length.*—Approximately 20.0 to 22.0 millimeters.

*Petal width.*—Approximately 15.5 to 16.5 millimeters.

Petal form: Considered broadly ovate.

Petal count: Nearly always 5.

Petal texture: Glabrous.

Petal color: Considered a light pink at the popcorn stage, (RHS Red-Purple Group 65 D), and darkening with advanced senescence, and the exposure to sunlight, to a medium-dark pink, (RHS Red-Purple 64 D).

Fragrance: Slight.

Petal claw:

*Form.*—The claw is considered ovate, and is generally medium in size.

*Length.*—Approximately 8.0-11.0 millimeters.

*Width.*—Approximately 6.0 to 7.5 millimeters.

Petal margins: Generally considered variable, from nearly smooth to slightly undulate.

Petal apex: Considered rounded.

Flower pedicel:

*Length.*—Considered medium with an approximate length of about 2.5 to about 3.0 millimeters.

*Diameter.*—Approximately 1.5 millimeters.

*Color.*—A medium brown, approximately (RHS Grey-Brown Group N199 D). This depends upon the pedicel and fruit maturity, and the timing of the visual observation.

*Surface texture.*—Glabrous.

Floral nectaries:

*Color.*—Considered a medium, and saturated orange, (approximately RHS Greyed-Orange Group 169 D).

Calyx:

*Surface texture.*—Generally glabrous.

*Color.*—A dull, browned-red, (approximately RHS Greyed-Red Group 178 A).

Sepals:

*Surface texture.*—The surface has a short, fine pubescent texture throughout the upper and lower surfaces.

*Sepal numbers.*—5 sepals are observed.

*Sepal size.*—Considered average.

*Sepal length.*—Approximately 8.0-10.0 millimeters.

*Sepal width.*—Approximately 5.0 to 7.0 millimeters.

*Sepal shape.*—Generally obovate.

*Sepal margin.*—Considered smooth, and entire.

*Sepal color.*—A dull grey-red, (approximately RHS Greyed-Red Group 178 B).

Position of stamen in relation to the petals: The stamen position is generally 4.0-6.5 mm superior to the petals.

Position of stigma relative to the stamens: The stigma position is generally 2.0-2.5 mm superior to the stamens.

Pubescence: The ovary is significantly pubescent.

Anthers:

*Generally.*—Considered average in size.

*Color.*—Orange when viewed dorsally, and prior to dehiscence, (approximately RHS Greyed-Orange Group 168 B).

Pollen production: Pollen is abundant, and has a yellow color, (approximately RHS Yellow-Orange Group 21 C).

Fertility: The new variety is considered self-fertile.

Filaments:

*Size.*—Approximately 10.0 to 12.0 millimeters in length.

*Color.*—Considered white to a pinkish-white, (RHS Red Purple Group 65 C).

Pistil:

*Number.*—Usually one, and only rarely more than one is observed.

*Generally.*—Large in size, and having a length of approximately 17.0 to about 20.0 millimeters including the ovary.

*Pistil color.*—Considered a very pale green, (approximately RHS Yellow-Green Group 154 D).

*Pistil surface texture.*—The variety has a long pubescent pistil.

FRUIT

Maturity when described: Firm ripe condition (shipping ripe).

Date of first picking: Approximately Sep. 23, 2015 under the prevailing ecological conditions as experienced in the Central Valley of California.

Date of last picking: Sep. 29, 2014. The date of harvest can vary with the prevailing climatic conditions, crop loads and the current climatic and horticultural practices which are employed.

Fruit size:

*Generally.*—Considered moderately large, and very uniform.

Average cheek diameter: Approximately 70.0 to about 78.0 millimeters.

Average axial diameter: Approximately 72.5 to about 76.0 millimeters.

Typical fruit weight: Approximately 270.0 grams. This characteristic is quite dependent upon the prevailing horticultural practices, and growing conditions, and therefore is not particularly distinctive characteristic of the new variety.

Fruit form:

*Generally.*—Considered globose. The fruit is generally very uniform in symmetry.

Fruit suture: No stitching exists along the suture line.

Suture:

*Color.*—Generally, the fruit appears blushed to the same degree as the skin, (approximately RHS Orange-Red Group N34 A).

Ventral surface:

*Form.*—Considered even, and uniform in appearance, when it is viewed from the lateral, sutural plane.

Apex:

*Shape.*—Generally rounded and occasionally appearing lobed.

Base:

*Shape.*—Generally flat.

Stem cavity:

*Generally.*—The stem cavity extends in a rounded circular form which is generally considered uniform. The stem cavity is rounded, but slightly extends toward the suture. The average depth of the stem cavity is about 7.0 to about 9.0 mm. The average length of the stem cavity, when measured in the sutural plane is about 50.0 mm.

Fruit skin:

*Thickness.*—Considered medium in thickness, and tenacious to the flesh.

*Surface texture.*—Short, fine and pubescent. The pubescence is moderately abundant.

*Taste.*—Non-astringent.

*Tendency to crack.*—Not observed in the previous years of observation, and evaluation.

Fruit skin color:

*Blush color.*—Generally speaking, a dull red blush exists on the skin of the fruit, (approximately RHS Greyed-Orange Group 175 B), and is more typically present on the portions of the fruit facing the sunlight. The blush of the fruit typically covers approximately 45%-65% of the fruit skin surface. The percentage of the blush on the fruit skin surface can vary, and is generally dependent upon the fruit's exposure to direct sunlight; specific fruit maturity; and also the prevailing ecological, and cultural conditions under which the fruit was grown.

Fruit blush skin pattern: Considered solid.

Ground color: A medium light yellow, (approximately RHS Yellow Group 13 B).

Fruit stem:

*Size.*—Medium in length, approximately 5.0 to about 8.0 millimeters.

*Diameter.*—Approximately 2.0 to about 3.0 millimeters.

*Color.*—Pale yellow-green, (approximately RHS Yellow-Green Group N144 C).

Fruit flesh:

*Ripening.*—Considered even.

*Flesh texture.*—Firm, crunchy, juicy and dense. Considered firm, yet non-melting.

*Flesh fibers.*—Present, but not prominent.

*Flesh aroma.*—Slight.

*Eating quality.*—Considered very good.

*Flesh flavor.*—Considered balanced, with both sweetness and acidity.

*Juice production.*—Considered moderate to abundant.

*Brix.*—About 14.0 to 17.0 degrees. This characteristic varies slightly with the number of fruit per tree; the maturity of fruit when harvested; the prevailing horticultural practices which are employed, and the ambient climatic conditions.

*Fruit acidity.*—Considered medium. Approximately 0.65 titratable acidity is observed. Acid levels assayed from fruit flesh can vary with fruit maturity, sunlight exposure, climatic variations, and regional and horticultural practices which are employed.

*Flesh color.*—The flesh is considered yellow in color, (approximately RHS Yellow Group 3 B). The flesh often exhibits red pigmentation which radiates from the stone, (approximately RHS Greyed-Red Group 179 A).

Firmness of the fruit flesh: Considered very firm.

STONE

Type: Considered a clingstone.

Stone size: It is generally considered to be medium large for the variety. The stone size varies significantly depending upon the tree vigor, the crop load, and the prevailing growing and horticultural conditions under which the tree was grown.

Stone length: On average, about 38.0 to about 42.0 millimeters.

Stone width: On average, about 24.0 to about 29.0 millimeters.

Stone diameter: On average, about 22.0 to about 26.0 millimeters.

Stone form: Roughly ovoid.

Stone base:

*Shape.*—The stone is considered shortly attenuate.

Stone apex:

*Shape.*—The stone exhibits a slightly acute apex.

Stone surface texture: Considered irregularly furrowed toward the apex. Further, more pitting exists in the mid-portion of the stone (laterally), and is more commonly observed toward the base.

*Ridges.*—Ridging is generally more prominent, and is usually oriented parallel, and laterally relative at the ventral and dorsal margins.

*Ventral edge.*—The ventral edge is generally considered troughed with three substantial grooves that converge apically.

*Dorsal edge.*—Shape — Generally considered even. The folds of the surface ridges appearing on the external margins often end gently along the suture.

Stone color: The color of a mature, dry stone is generally considered a dull brown, approximately (RHS Greyed-Orange Group 166 C).

Tendency to split: Splitting has rarely been observed.

Kernel:

*Length.*—Approximately 19.0-21.0 millimeters.

*Width.*—Approximately 13.0-15.0 millimeters.

*Thickness.*—5.0-6.0 millimeters.

*Size.*—The kernel is considered medium in size.

*Form.*—Considered generally ovoid.

*Pellicle.*—Slightly pubescent.

*Color.*—A dark tan (RHS Greyed-Orange Group 165 B).

Use: The present variety 'Burpeachthirtyseven' is considered to be a peach tree of the late season of maturity, and which produces fruit which are considered to be firm, attractively colored, and which are useful for both local and long distance shipping.

Keeping quality: Appears excellent. The fruit of the present variety has stored well for periods of up to 35 days after harvest at 1.0 degree Celsius.

Shipping quality: Good. The fruit of the new peach tree variety showed minimal bruising of the flesh or skin damage after being subjected to normal harvesting and packing procedures.

Resistance to insects and disease: No particular susceptibilities were noted. The present variety has not been intentionally tested to expose or detect any susceptibilities or resistances to any known plant, fruit diseases, insect, frost, winter injury or other environmental factors.

Although the new variety of peach tree possesses the described characteristics when grown under the ecological conditions prevailing near Fowler, Calif., in the Central part of the San Joaquin Valley of California, it should be understood that variations of the usual magnitude, and characteristics incident to changes in growing conditions, fertilization, nutrition, pruning, pest control, frost, climatic variables and changes in horticultural management are to be expected.

Having thus described and illustrated our new variety of peach tree, what we claim is new, and desire to secure by plant Letters Patent is:

1. A new distinct variety of peach tree, substantially as illustrated and described, and which is characterized principally as to novelty by producing an attractively colored yellow fleshed, clingstone peach which is mature for harvesting and shipment approximately September 23 to September 29 under the ecological conditions prevailing in the San Joaquin Valley of central California.

* * * * *

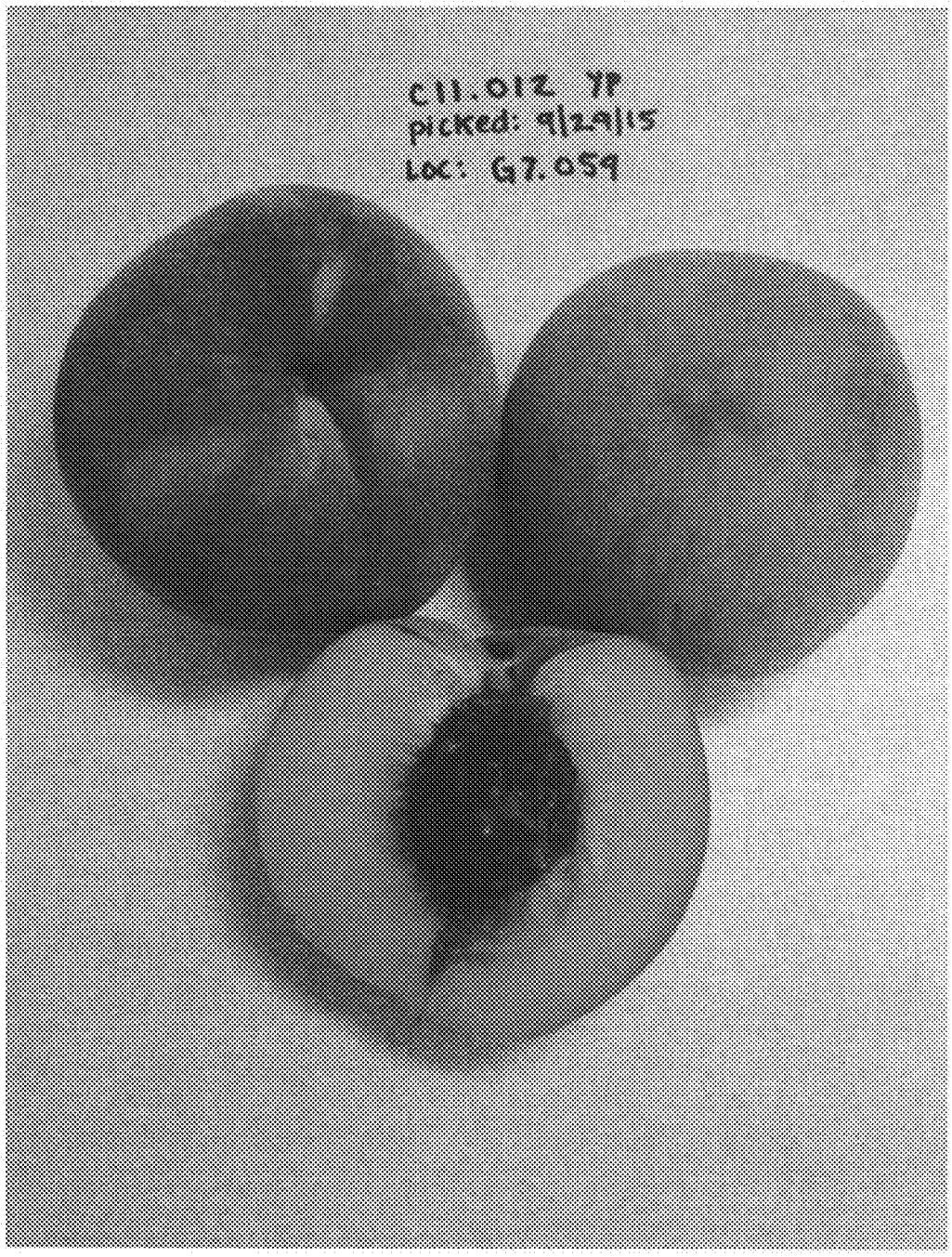
C11.012 YP
picked: 9/29/15
Loc: G7.059